(12) United States Patent
Albertal

(10) Patent No.: US 10,716,587 B2
(45) Date of Patent: Jul. 21, 2020

(54) SURGICAL DEVICE WITH LIGHT

(71) Applicant: Jorge Manuel Albertal, Buenos Aires (AR)

(72) Inventor: Jorge Manuel Albertal, Buenos Aires (AR)

(73) Assignee: Surgis Medical LLC, Lewes, DE (US)

( * ) Notice: Subject to any disclaimer, the term of this patent is extended or adjusted under 35 U.S.C. 154(b) by 0 days.

(21) Appl. No.: 14/738,878

(22) Filed: Jun. 13, 2015

(65) Prior Publication Data

US 2015/0359581 A1  Dec. 17, 2015

Related U.S. Application Data

(60) Provisional application No. 62/012,216, filed on Jun. 13, 2014.

(51) Int. Cl.

| | |
|---|---|
| *A61B 17/28* | (2006.01) |
| *A61B 90/30* | (2016.01) |
| *A61B 18/14* | (2006.01) |
| *A61B 90/00* | (2016.01) |

(52) U.S. Cl.
CPC .......... *A61B 17/2812* (2013.01); *A61B 18/14* (2013.01); *A61B 90/30* (2016.02); *A61B 18/148* (2013.01); *A61B 18/1477* (2013.01); *A61B 90/361* (2016.02); *A61B 2018/1407* (2013.01); *A61B 2018/1412* (2013.01); *A61B 2018/1462* (2013.01); *A61B 2090/309* (2016.02); *A61B 2218/007* (2013.01)

(58) Field of Classification Search
CPC .... A61B 2018/1412; A61B 2018/1422; A61B 2018/1432; A61B 2018/1415
See application file for complete search history.

(56) References Cited

U.S. PATENT DOCUMENTS

| | | | |
|---|---|---|---|
| 1,038,011 A * | 9/1912 | Snell | A61B 1/06 362/120 |
| 2,002,594 A | 5/1935 | Wappler et al. | |

(Continued)

FOREIGN PATENT DOCUMENTS

WO    WO/2009/031995 A1    3/2009

*Primary Examiner* — Ronald Hupczey, Jr.
(74) *Attorney, Agent, or Firm* — Lee & Lin IP, PLLC; Jeong Eun Lee-Nago; Rita H. Lin

(57) ABSTRACT

An electrocautery unit for connecting to a handle of an electrocautery device, the unit comprises a body, a light unit and an electrode. The body has a body proximal end and a body distal end, and a body axis extending lengthwise along the center of the body. The body's proximal end comprises a connecting element for connecting said body to a handle having a handle axis extending lengthwise along the center of the handle, so that said body axis is coaxial with said handle axis when said body is connected to said handle. The light unit may be constructed and arranged to emit a light having a central axis coaxial with said body axis. The electrode comprises a proximate end connected to the body distal end, and an electrode tip at a distal said. When the electrode is connected to the body, the electrode lays outside of the body axis and extends into said body axis such that the electrode tip is within said body axis, wherein said light and said electrode tip are coaxial to said body axis and said handle axis.

32 Claims, 15 Drawing Sheets

(56) References Cited

U.S. PATENT DOCUMENTS

| | | | |
|---|---|---|---|
| 2,029,487 A * | 2/1936 | Kleine | A61B 18/10 362/119 |
| 2,031,682 A | 2/1936 | Wappler et al. | |
| 2,102,270 A | 12/1937 | Hyams | |
| 2,196,171 A | 4/1940 | Arnesen | |
| 2,224,464 A * | 12/1940 | Wolf | A61B 1/2676 600/104 |
| 3,058,470 A | 10/1962 | Seeliger | |
| 3,219,029 A | 11/1965 | Richards | |
| 3,460,539 A | 8/1969 | Anhalt, Sr. | |
| 3,648,001 A | 3/1972 | Anderson | |
| 3,720,896 A | 3/1973 | Beierlein | |
| 3,825,004 A | 7/1974 | Durden, III | |
| 3,828,780 A | 8/1974 | Morrison, Jr. | |
| 3,875,945 A | 4/1975 | Friedman | |
| 3,902,494 A | 9/1975 | Haberlen | |
| 3,906,955 A | 9/1975 | Roberts | |
| 3,939,839 A * | 2/1976 | Curtiss | A61B 1/12 600/105 |
| 3,974,833 A | 8/1976 | Durden, III | |
| 4,032,738 A | 6/1977 | Esty | |
| 4,034,761 A | 7/1977 | Prater | |
| 4,112,950 A | 9/1978 | Pike | |
| D253,247 S | 10/1979 | Gill | |
| 4,232,676 A | 11/1980 | Herczog | |
| 4,273,109 A * | 6/1981 | Enderby | A61B 18/24 219/121.6 |
| 4,273,127 A * | 6/1981 | Auth | A61B 17/3211 219/121.6 |
| 4,314,559 A | 2/1982 | Allen | |
| 4,427,006 A | 1/1984 | Nottke | |
| 4,492,231 A | 1/1985 | Auth | |
| 4,542,741 A * | 9/1985 | Burgin | A61B 17/3211 362/119 |
| 4,545,375 A | 10/1985 | Cline | |
| 4,562,838 A | 1/1986 | Walker | |
| 4,589,411 A | 5/1986 | Friedman | |
| 4,593,691 A | 6/1986 | Lindstrom et al. | |
| 4,595,809 A | 6/1986 | Pool | |
| 4,606,342 A | 8/1986 | Zamba | |
| 4,619,258 A | 10/1986 | Pool | |
| 4,625,723 A | 12/1986 | Altnether | |
| 4,640,279 A | 2/1987 | Beard | |
| 4,657,016 A | 4/1987 | Garito | |
| 4,688,569 A * | 8/1987 | Rabinowitz | A61B 18/1402 606/37 |
| 4,754,754 A | 7/1988 | Garito | |
| 4,785,807 A | 11/1988 | Blanch | |
| 4,803,323 A | 2/1989 | Bauer | |
| 4,811,733 A | 3/1989 | Borsanyi | |
| D301,739 S | 6/1989 | Turner et al. | |
| 4,840,563 A * | 6/1989 | Altendorf | A61C 17/20 174/36 |
| 4,850,353 A | 7/1989 | Stasz | |
| 4,862,890 A | 9/1989 | Stasz | |
| 4,876,110 A | 10/1989 | Blanch | |
| 4,901,719 A | 2/1990 | Trenconsky | |
| 4,909,249 A | 3/1990 | Akkas | |
| 4,911,159 A | 3/1990 | Johnson | |
| 4,919,129 A | 4/1990 | Weber, Jr. et al. | |
| 4,922,903 A | 5/1990 | Welch | |
| 5,011,483 A | 4/1991 | Sleister | |
| 5,035,695 A | 7/1991 | Weber, Jr. et al. | |
| 5,055,100 A | 10/1991 | Olsen | |
| 5,071,418 A | 12/1991 | Rosenbaum | |
| 5,076,276 A | 12/1991 | Sakurai et al. | |
| 5,078,712 A * | 1/1992 | Easley | A61B 18/1402 606/16 |
| 5,246,440 A | 9/1993 | Van Noord | |
| 5,454,115 A * | 9/1995 | Okamoto | G06F 15/82 712/215 |
| 5,531,743 A * | 7/1996 | Nettekoven | A61B 18/14 606/41 |
| 5,542,945 A * | 8/1996 | Fritzsch | A61B 18/14 606/41 |
| 5,951,550 A | 9/1999 | Shirley | |
| 6,562,032 B1 * | 5/2003 | Ellman | A61B 17/320068 606/41 |
| 8,287,534 B2 | 10/2012 | Balog | |
| 8,506,565 B2 | 8/2013 | DeCarlo | |
| 8,529,564 B2 | 9/2013 | Wu | |
| 8,795,162 B2 | 8/2014 | Vayser | |
| 2002/0058931 A1 | 5/2002 | Parker | |
| 2003/0195559 A1 | 10/2003 | Colgan | |
| 2004/0097916 A1 | 5/2004 | Thompson | |
| 2005/0171408 A1* | 8/2005 | Parker | A61B 17/02 600/249 |
| 2006/0069386 A1* | 3/2006 | Dubnack | A61B 18/1402 606/41 |
| 2006/0291195 A1 | 12/2006 | Horrell | |
| 2007/0049927 A1 | 3/2007 | Saltzman | |
| 2008/0147058 A1 | 6/2008 | Horrell | |
| 2010/0125172 A1 | 5/2010 | Jayaraj | |
| 2010/0145333 A1 | 6/2010 | Dethier | |
| 2011/0060332 A1 | 3/2011 | Cheng | |
| 2012/0157326 A1 | 6/2012 | Tisi | |
| 2012/0283718 A1* | 11/2012 | Cosmescu | A61B 18/1402 606/33 |
| 2012/0316553 A1* | 12/2012 | Balog | A61B 18/1402 606/33 |
| 2013/0103032 A1* | 4/2013 | Beaven | A61B 18/1482 606/48 |
| 2013/0267787 A1 | 10/2013 | Warnock | |

* cited by examiner

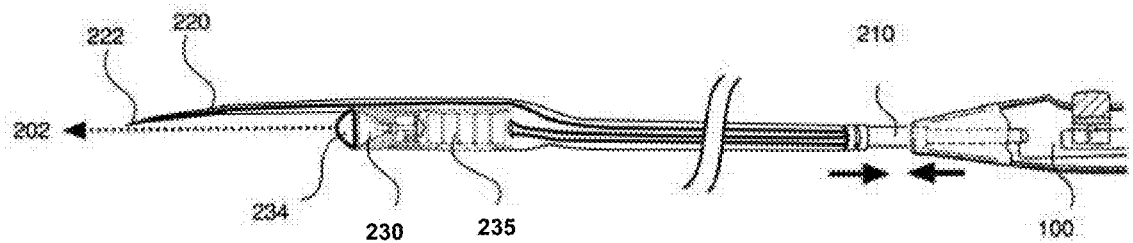
Fig. 3
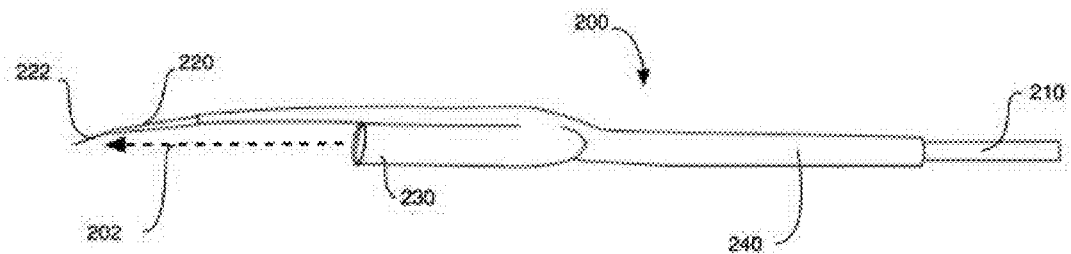
Fig. 4
Fig. 5
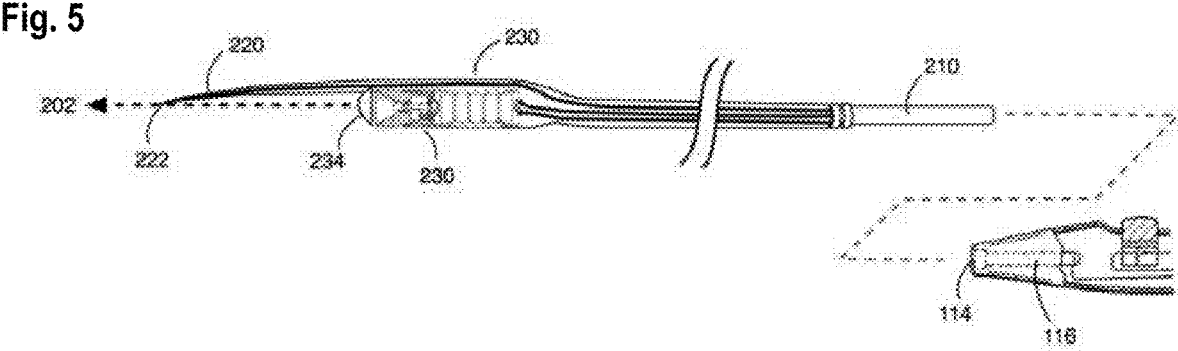

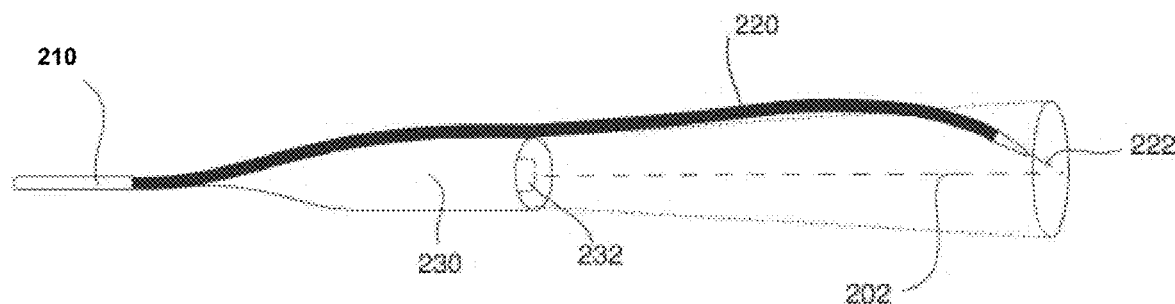
Fig. 6A
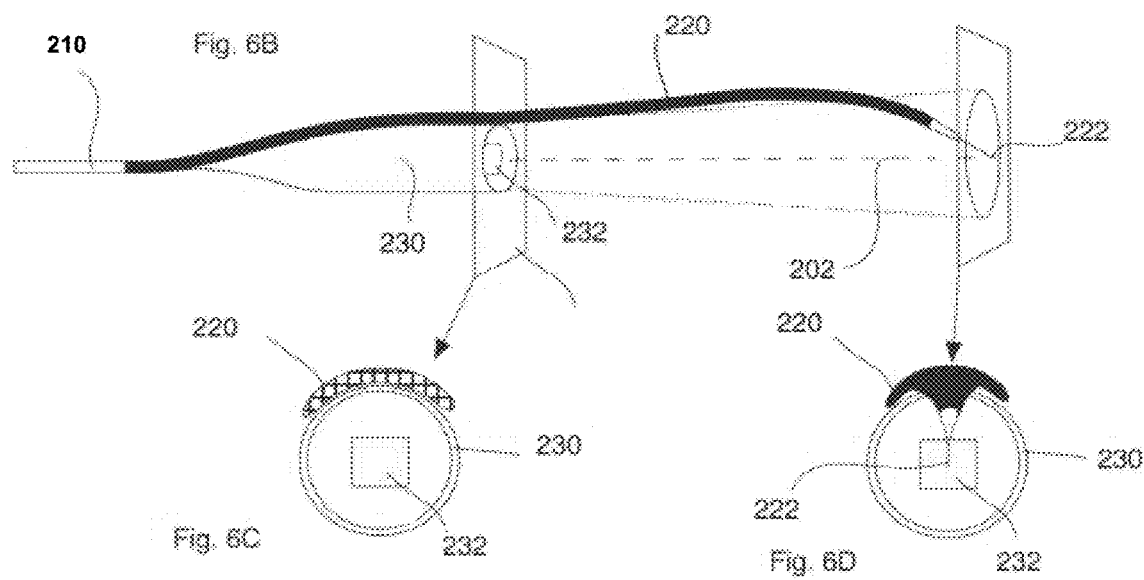
Fig. 6B
Fig. 6C
Fig. 6D

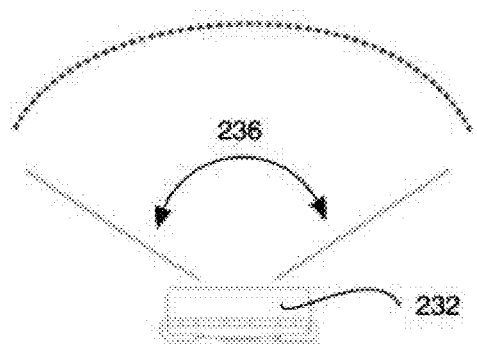
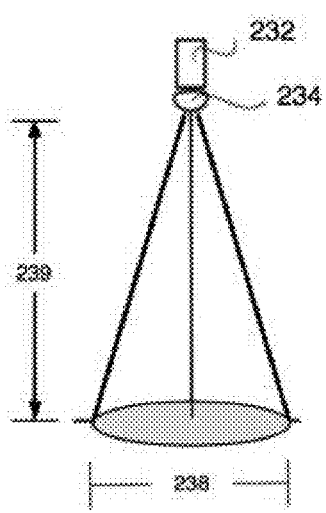
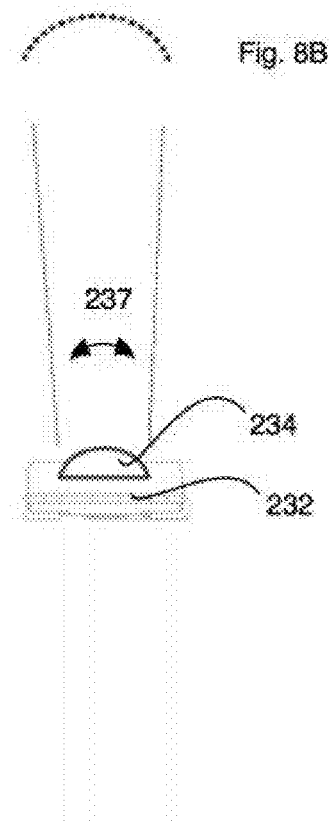

SURGICAL DEVICE WITH LIGHT

CROSS REFERENCE TO RELATED APPLICATION

The application claims the benefit of U.S. Provisional Application No. 62/012,216 titled "A Surgical Lighting Hand-Piece Device with Electrocautery and Video Capabilities," filed Jun. 13, 2014, which is incorporated by reference herein in its entirety.

FIELD OF INVENTION

The present invention is related generally to a medical apparatus and an electrocautery system and particularly to electrocautery tools having a lighting component to provide light during deep surgical procedures.

BACKGROUND OF THE INVENTION

Proper lighting is a critical component of any operating room. Surgeons need ample lighting to illuminate the area on which the procedure is taking place. Modern surgery has evolved continuously to smaller opening incisions and more complex operating sites, all with the objective of leaving smaller scars and creating less discomfort for the patient. For example, in cosmetic surgery, among others, there is a need to perform better and more precise dissection between tissue layers deep in the site and a rising demand for better surgical tools to facilitate the surgeon's work and improve teaching skills. Electrocautery devices are often utilized to cauterize wounds, stop bleeding, or excise tissue.

To provide the needed illumination for increasingly complex surgeries, lighting in operating rooms has evolved from bulky overhead, adjustable lighting that can be shifted to point the light beam from different angles to headlamps worn on the heads of the surgeons or surrounding staff, to having a small lighting unit built into electrocautery that surgeons use to operate on patients.

Both overhead lighting and headlamp approach provide sufficient ambient lighting during surgery, but often fail at specifically illuminating the targeted deep field site. The adjustability of the overhead lighting is limited by its fixed position on the ceiling and its ability to be extended downward from the ceiling without hindering the surgeon's vision or movement. The headlamp approach allows the light to move with the surgeon, but requires the surgeon to tilt his head or adjust and maintain his body position to point the lamp at the targeted area. Even with these extra movements, which increase the possibility of error, the bulk of the light from headlamps are blocked and/or reflected by the skin around the small incision and fails to penetrate the skin and illuminate the inside of the incision where the surgical procedure is taking place.

Whereas certain electrocautery devices exist with built-in lighting components that attempt to carry the light pass the skin around the incision opening, they each have drawbacks that are addressed by the invention described herein. Since the internal construction of the human body is extremely complex, in order for a surgeon to properly and safely perform a more precise dissection between deep-site tissue layers, a more concentrated and pinpointed lighting is critical to aid the surgeon in cutting, dissection and cauterization. A lack of sufficient light at the treatment site within the patient's body may cause the doctor to accidentally injure other parts of the patient's body. Since electrocautery generally requires controlled application of radiofrequency energy to an operative tissue site, it is important that the site be properly illuminated for the surgeon to operate.

Better lighting inside the incision is also preferred for teaching purposes, both to point out the targeted area and also to illuminate the area when utilizing a camera or other audio-visual device to facilitate demonstrating the procedure to students.

Accordingly, it is desirable to provide an improved electrocautery apparatus and system to provide light that overcomes drawbacks and inadequacies of known methods and systems.

SUMMARY OF THE INVENTIONS

Generally speaking, in accordance with an embodiment of the invention, an electrocautery unit comprises a body, a light unit and an electrode. The proximal end of the body may be connected to a handle. The distal end of the body may be connected to the electrode. The body and the handle are generally coaxial lengthwise along the center of the body and the center of the handle. The light unit emits light that is also coaxial to the center of the body and the center of the handle. However, the electrode is constructed and arranged to lie outside of the co-axis of the body and the handle and extends into the co-axis only at its distal end where the electrode tip is located. Specifically, the electrode tip is coaxial to the center of the body and the center of the handle, as well as the light mitted.

An embodiment of the invention provides an electrocautery kit comprising an elongated body having multiple connecting elements and an electrode. The body has a first connecting element constructed and arranged to connect to a handle of an electrocautery device, a second connecting element to connect to the electrode in the kit. The body further comprises a light element constructed and arranged to emit a light that is coaxial to the body's central axis lengthwise. When the electrode is connected to the body, the electrode's central axis is not coaxial with the body's central axis. However the electrode is constructed and arranged to have an electrode tip that extends toward the central axis of the body.

Another embodiment of the invention is directed to a pair of forceps having a light unit and a camera unit.

Yet another embodiment of the invention is directed to an electrocautery unit having a camera.

Still other objects and advantages of the invention will in part be obvious and will in part be apparent from the specification. Other features and advantages of this invention will become apparent in the following detailed description of exemplary embodiments of this invention with reference to the accompanying drawings.

BRIEF DESCRIPTION OF THE DRAWINGS

For a fuller understanding of the invention, reference is made to the following description taken in connection with the accompanying drawing, in which:

FIG. 3 is a side view of an electrocautery device in accordance with an embodiment of the invention;

FIG. 4 is a side view of an electrode unit in accordance with an embodiment of the invention;

FIG. 5 is cross sectional view of the electrode unit of FIG. 4 detached from an embodiment of a handle;

FIG. 6A is a side view of an electrode unit illustrating the central axis projected from a light element coaxial with the tip of the electrode in accordance with an embodiment of the invention;

FIG. 6B is a side view of an electrode unit illustrating the central axis projected from a light element coaxial with the tip of the electrode in accordance with an embodiment of the invention;

FIG. 6C is the cross sectional view of the embodiment of FIG. 6B taken along plane A;

FIG. 6D is the front view of the embodiment of FIG. 6B;

FIG. 7 is a diagram showing the field of illumination of a lighting element with a lens in accordance with an embodiment of the invention;

FIG. 8A is a side view of a light element in accordance with an embodiment of the invention, showing the angle of illumination of the light element without a lens;

FIG. 8B is a side view of the light element of 8A with a lens, showing the angle of illumination of the light;

FIG. 16A is a perspective view of a removable electrode having a camera with an handle in accordance with an embodiment of the;

FIG. 16B is a perspective of the embodiment of FIG. 16A having a shaft;

DETAILED DESCRIPTION OF THE PREFERRED EMBODIMENTS

Figure 1:
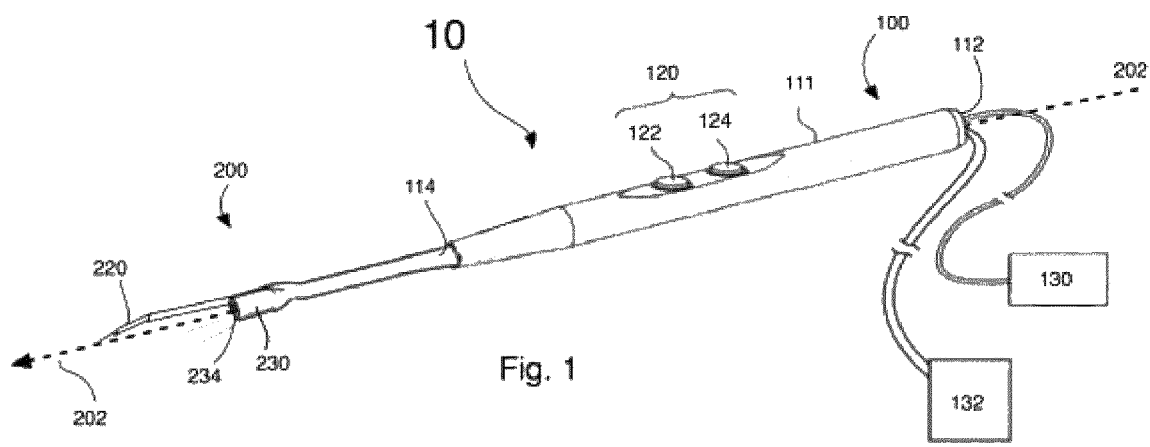
FIG. 1 is a perspective view of an electrocautery device in accordance with an embodiment of the invention.
Figure 2:
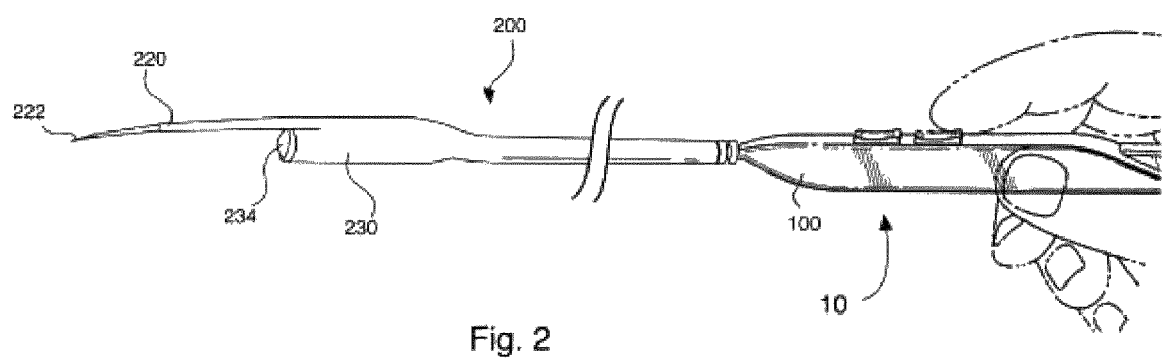
FIG. 2 is a side view of an electrocautery device in accordance with an embodiment of the invention.

Certain exemplary embodiments of the present invention will now be described with reference to the drawings. Reference is made to FIGS. 1-16B, in which certain embodiments of the invention are shown. Generally, an electrocautery device 10 includes a handle 100 and a blade unit 200, 300, 400, 500 having a coupling element 210, 310, 410, 510 for removably connecting to handle 100, such that the same handle 100 may be used with a variety of blade units 200, 300, 400, 500. More preferably, handle 100 is a standard electrocautery handle, such that blade unit 200, 300, 400, 500 retrofits electrocautery handles currently available.

In the embodiments illustrated, coupling element 210, 310, 410, 510 includes a male connector constructed and arranged to be inserted into handle 100. However, it is to be understood that the coupling element may include a female receiving portion for receiving a male connector of the handle, or other coupling mechanisms, such as a threated mechanism, a friction fit mechanism, male-female flange and groove, etc. are contemplated without deviating from the scope of the invention. Moreover, although the illustrated embodiment of coupling element 210, 310, 410, 510 has a round, rod-like shape, it may be square or take on any other shape or size suitable for connecting with handle 100.

Blade Unit

Figure 17:
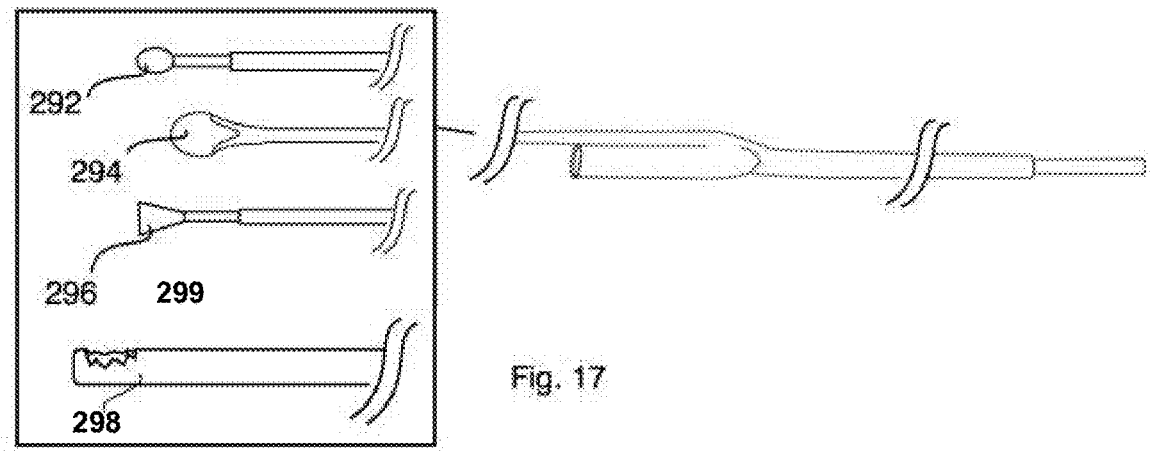
FIG. 17 is a diagram showing various electrode tips in accordance with an embodiment of the invention.
Figure 18:
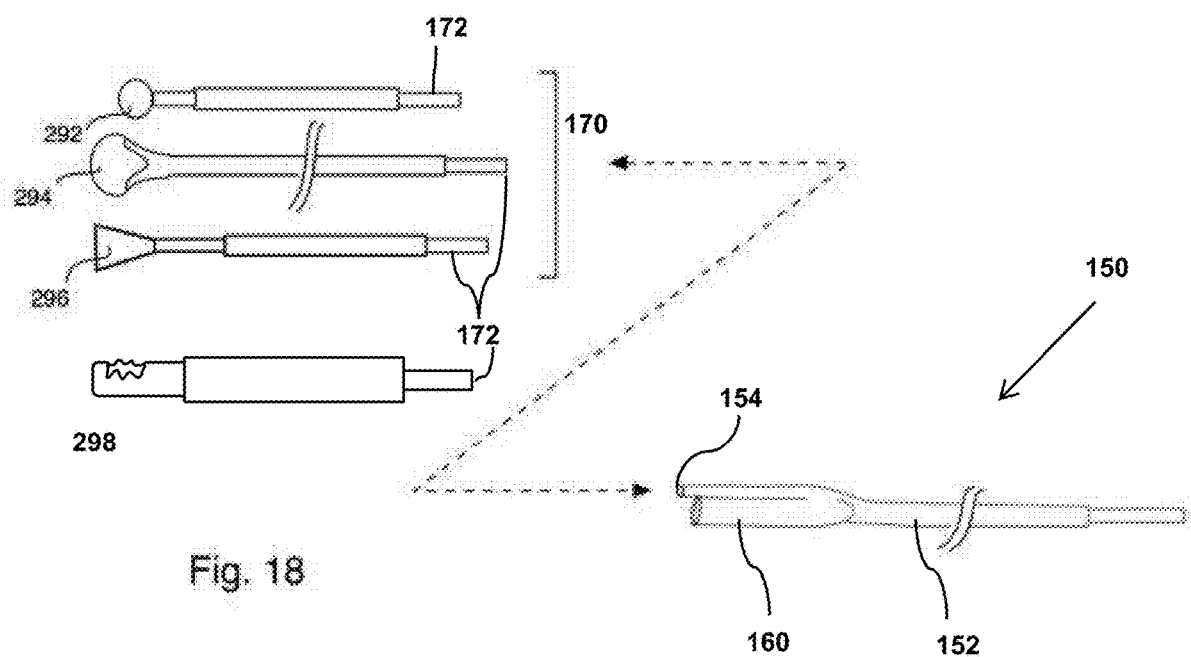
FIG. 18 is showing the electrode tips of FIG. 17 detached from an embodiment of a handle.

Blade unit 200, 300, 400, 500 preferably includes a surgical electrode 220, 320, 420, 520, a lighting element 230, 330, 430, 530 and a shaft extending between lighting element 230, 330, 430, 530 and coupling element 210, 310, 410, 510. Generally speaking, the surgical electrode 220, 320, 420, 520 includes an electrode tip 222, 322, 422, 522 and comprises a material that conducts electricity, such as metal, via which a current is transferred to the tissue of the patient, for example, for electrocauterization. The surgical electrode 220, 320, 420, 520 may have various shapes and sizes according to the desired surgical procedure. For example, surgical electrode 220, 320, 420, 520 may be a blade for cutting, and the specific size and shape of the blade may differ depending on the location of the surgery and the type of tissue to be cut. Whereas the embodiments illustrated include a bayonet-shaped electrode 220, 320, 420, 520, the electrode may be curved, angular or any other shape, preferably with the electrode tip curving toward axis 202, 302, 402, 502 such that the electrode tip is located along said axis. The surgical electrode may alternatively be a uterus wall cutter 296 or other cutter 294, or probe 292, 298 as shown in FIGS. 17-18. As shown, the device may comprise a variety of components not limited to a blade or cutter, such as a probe 292, 298. Cutter 294, 296 or probe 292, 298 is preferably structured and arranged such that the tip of cutter 294, 296 or probe 292, 298 is positioned coaxial with the light emitted by the lighting element, and more preferably, coaxial with the handle to which the device is connected. A first probe 292 may comprise a rounded tip, whereas a second probe 298 may include an opening designed to cut or destroy tissue.

In accordance with an embodiment of the invention shown in FIG. 18, the blade unit 150 includes a lighting element 160 that is fixed to base 152 of blade unit 150, and a removable electrode 170, which preferably comprise a variety of cutters 294, 296 or probes 292, 298. Preferably, removable electrode 170 includes a coupling element 172 for engaging a corresponding coupling element 154 of base 152. Thus, the same base 152 may be used for a variety of procedures, simply by attaching the desired electrode, blade, tip, etc.

Whereas the examples of cutters are described herein are directed toward electrodes using heat, it is to be understood that a blade or other means for cutting without heat may be provided without deviating from the scope of the invention.

Lighting element 230, 330, 430, 530, preferably includes a light source 232, by way of non-limiting example, one or more light-emitting diodes (LED). The example illustrated in FIGS. 7 and 8A-8B shows light source 232 comprising an LED. Lighting element 230, 330, 430, 530 is preferably configured to provide an angle of illumination 237 having an angle of between approximately 10 and 40 degrees, more preferably approximately 20 and 30 degrees. Light source 232 may provide the desired angle of illumination 237 or lighting element 230, 330, 430, 530 may include a lens 234, 334, 434, 534, preferably a convex lens, to reduce the original angle of illumination 236 of light source 232 to the desired angle of illumination 237, as illustrated in FIGS. 8A and 8B. In the example shown, light source 232 is an LED having an original angle of dispersion 236 of 120 degrees, which convex lens 234 reduces to 30 degrees by refracting the light passing through it.

A narrower angle of illumination should reduce the size of the field of illumination, namely the area illuminated. Preferably, the field of illumination proximate electrode tip 222, 322, 422, 522 has a diameter 238 of between approximately 2.5 and 6.5 cm, more preferably approximately 4.5 cm or less, at a distance 239 from lighting element 230, 330, 430, 530, distance 239 being preferably between approximately 1 and 7 cm, more preferably between approximately 2 and 5 cm, most preferably approximately 3 cm. In accordance with an embodiment of the invention, lens 234 may be adjusted, for example, turned or shifted, to focus the light or adjust diameter 238 of the field of illumination.

Figure 9:
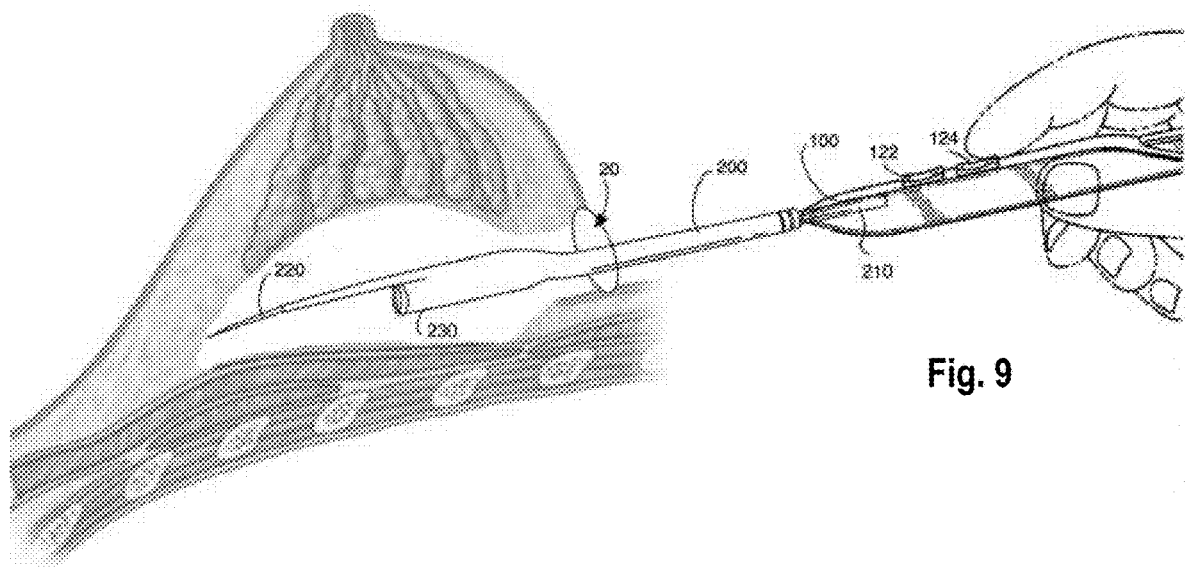
FIG. 9 is a diagram illustrating an electrocautery device in accordance with an embodiment of the invention held by a user's hand and being inserted into the opening of an incision during a surgical procedure.
Figure 10:
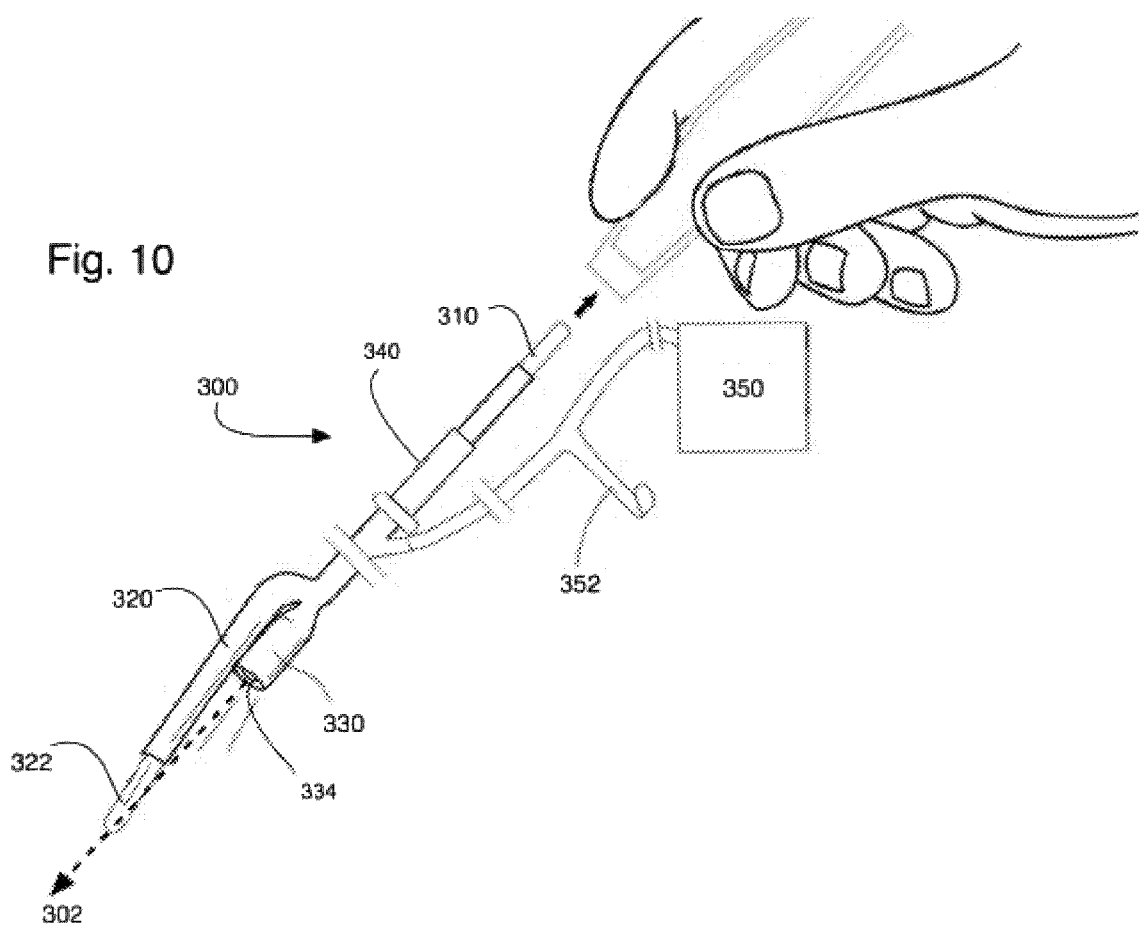
FIG. 10 is a side view of an electrocautery device in accordance with an embodiment of the invention having a securing element.
Figure 11:
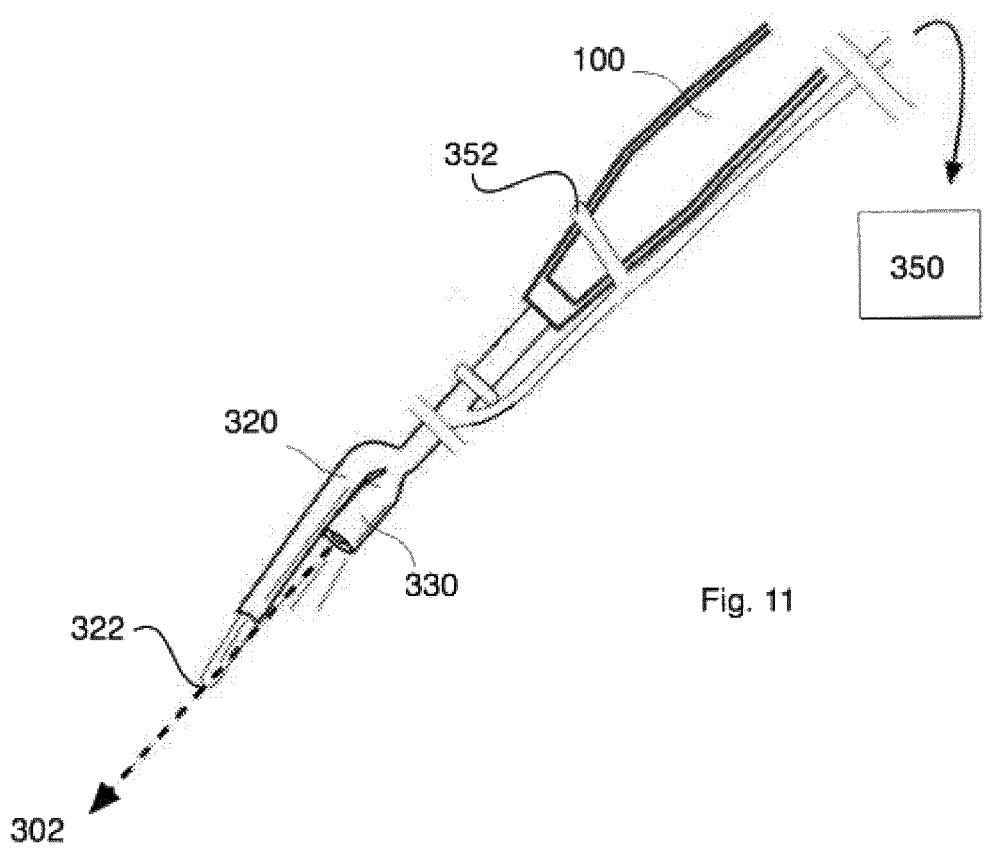
FIG. 11 is a side view of an electrocautery device in accordance with an embodiment of the invention having an independent power source for the light element.

Moreover, blade unit 200, 300, 400, 500 is preferably constructed and arranged such that electrode tip 222, 322, 422, 522 is between approximately 5 cm from lighting element 230, 330, 430, 530, permitting the light source to be brought past the skin at incision 20 and into the pocket as illustrated in FIG. 9. As described above, many surgeries call for small incisions to minimize scarring, reduce patient's discomfort, because of the complex surgical sites, etc. In the embodiment illustrated, incision 20 is not much larger than the cross-section of device 10. Thus, device 10 can be inserted through incision 20 and avoids light from lighting element 230 being reflected on the outer skin of the patient around incision 20 and the associate glare therefrom, which are some drawbacks of headlamps and other external light sources. Additionally, a greater amount of light reaches the surgical site, since the entire light source is within the pocket, which facilitates the focal vision of the operator, and facilitates recording by a camera within the pocket.

Preferably, the distance between the blade tip and the light source for blades longer than the examples illustrated are also approximately 5 cm, thus not sacrificing the concentration of light just because of the length of the blade. Additionally, whereas light source 232 is illustrated as being fixed, it may be adjustable within lighting element 230, for example, moved to vary the intensity of the light, without deviating from the scope of the invention. Likewise, lighting element 230, 330, 430, 530 may be adjustable, for example, rotatable, slidable, removable, etc. with respect to blade unit 200, 300, 400, 500 without deviating from the scope of the invention.

Figure 21A:
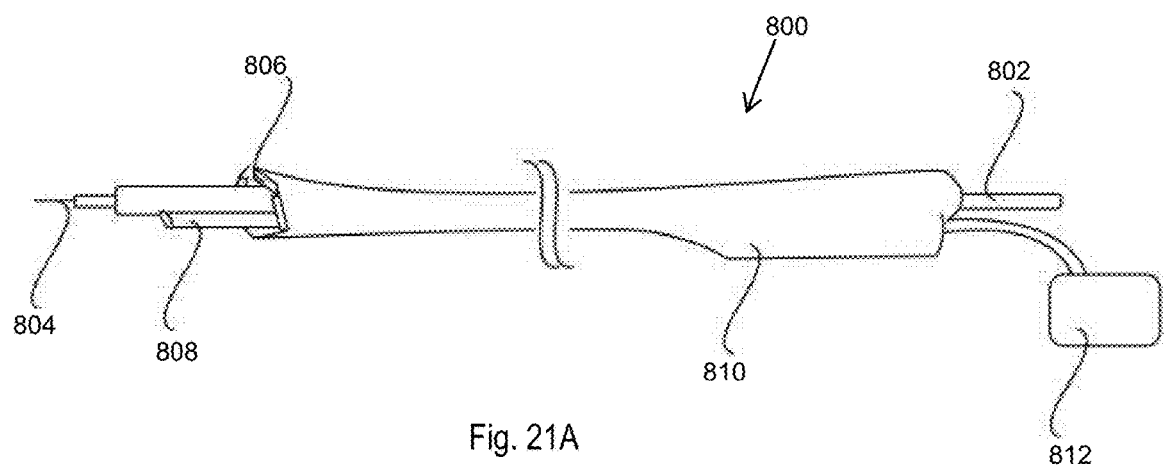
FIG. 21A is a side view of an electrocautery device with a suction element in accordance with an embodiment of the invention.
Figure 21B:
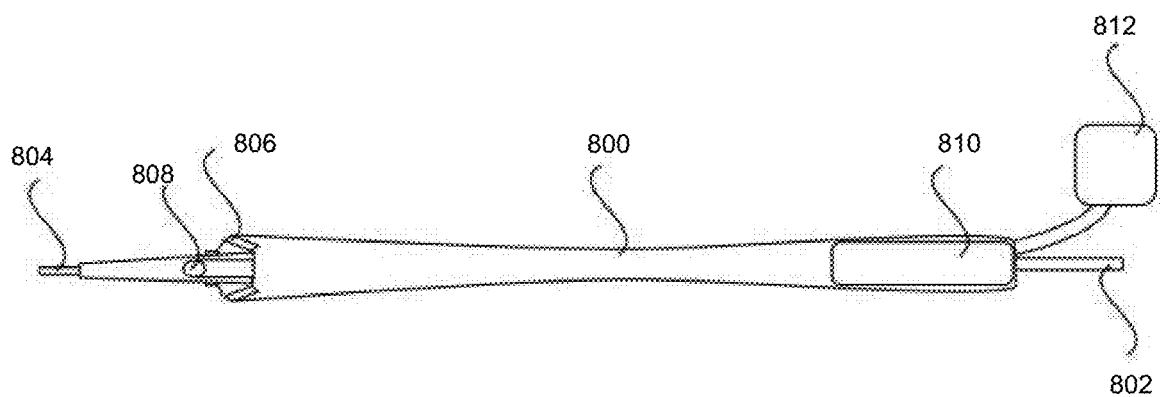
FIG. 21B is a side view of the electrocautery device of FIG. 21A showing with a battery proximate the light unit.
Figure 21C:
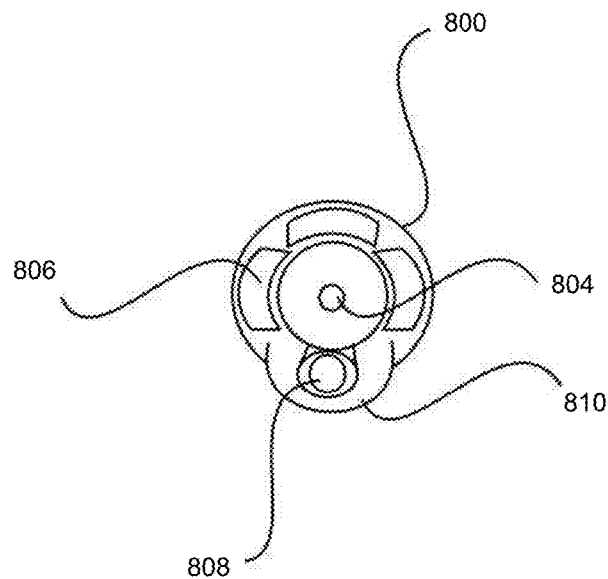
FIG. 21C is a front view of the electrocautery device of FIG. 21A.
Figure 22A:
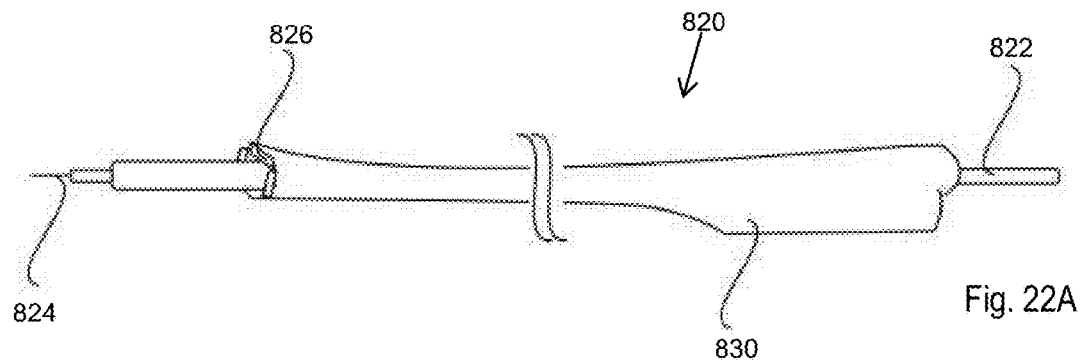
FIG. 22A is a side view of an electrocautery device having multiple light elements and a built it power source as in accordance with an embodiment of the invention.
Figure 22B:
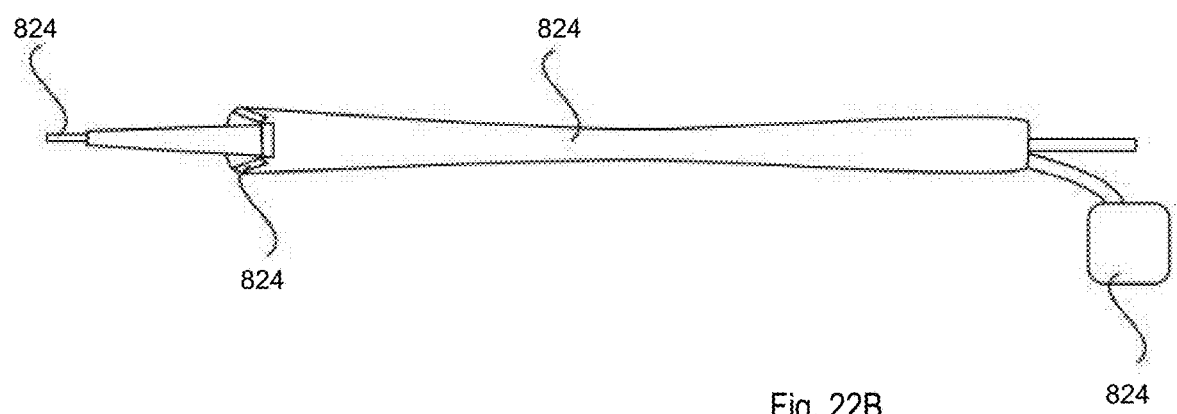
FIG. 22B is a side view of an electrocautery device having multiple light elements and an external power source as in accordance with an embodiment of the invention.
Figure 22C:
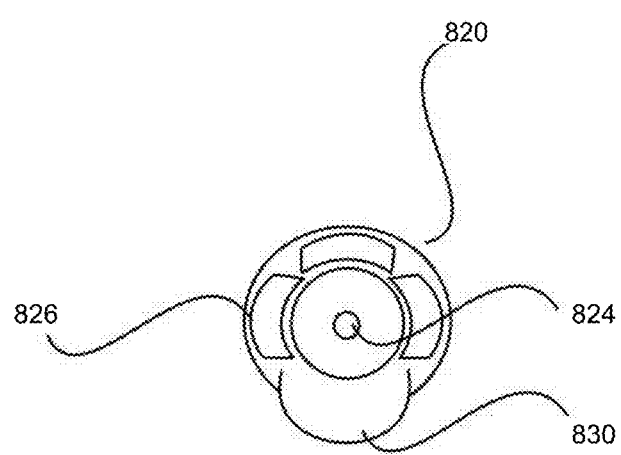
FIG. 22C is front view of electrocautery device of FIG. 22A.

Lighting element 230, 330, 430, 530 provides a sufficiently bright illumination to provide the surgeon with sufficient light to see the tissue being operated on, preferably between 3,000 to 6,000 millicandela (MCD). Moreover, it is preferred for lighting element 230, 330, 430, 530 or other part of blade unit 200, 300, 400, 500 to include a heat diffuser to avoid burning the tissue of the patient. Blade unit 200, 300, 400, 500 may also include a smoke and/or blood removal mechanism as well, as illustrated in FIG. 21A-21C.

Whereas the example of light source 232 is an LED, it is to be understood that various sources of light may be used, depending on the desired size, color, temperature, amount of heat it emits, current, etc.

In the embodiment shown, coupling element 210, 310, 410, 510 is constructed and arranged such that when blade unit 200, 300, 400, 500 is connected to handle 100, handle 100 is coaxial along axis 202, 302, 402, 502 with lighting element 230, 330, 430, 530. Furthermore, lighting element 230, 330, 430, 530 emits light having a central axis coinciding with axis 202, 302, 402, 502, and electrode tip 222, 322, 422, 522 is positioned along axis 202, 302, 402, 502. Hence, wherever handle 100 is pointed, the light emitted from lighting element 230, 330, 430, 530 and electrode tip 222, 322, 422, 522 will be moved there as well.

Preferably, the surgical electrode 220, 320, 420, 520 is shaped and arranged such that only electrode tip 222, 322, 422, 522 lies along axis 202, 302, 402, 502, thus minimizing, if not eliminating, shadows cast by surgical electrode 220, 320, 420, 520. In the embodiment shown, surgical electrode 220, 320, 420, 520 is elongated, extending away from the distal end of handle 100, alongside and past lighting element 230, 330, 430, 530, after which electrode tip 222, 322, 422, 522 juts toward axis 202, 302, 402, 502. Therefore, when the surgeon or other user directs handle 100 to point the light toward the desired area, electrode tip 222, 322, 422, 522 is also moved to the desired area to perform the procedure. Furthermore, such an arrangement of blade unit 200, 300, 400, 500 may permit procedures to be conducted deeper in a patient's body, since light can reach deeper within the body compared to when using headlamps and overhead light.

More preferably, a shaft 240, 340, 440, 540 extends between lighting element 230, 330, 430, 530 and coupling element 210, 310, 410, 510, wherein lighting element 230, 330, 430, 530 and shaft 240, 340, 440, 540 are coaxial along axis 202, 302, 402, 502.

Handle

The illustrated embodiment of handle 100 comprises an elongated body 111, a proximal end 112 having wires or other connection means to connect to an electrode power source 130, and a distal end 114 having a handle coupling element 116 for connecting to coupling element 210, 310, 410, 510 of blade unit 200, 300, 400, 500. In the embodiments illustrated, handle coupling element 116 comprises a receiving cavity for receiving coupling element 210 of blade unit 200 and electrically connecting thereto, thus transmitting electricity to blade unit 200.

Figure 12:
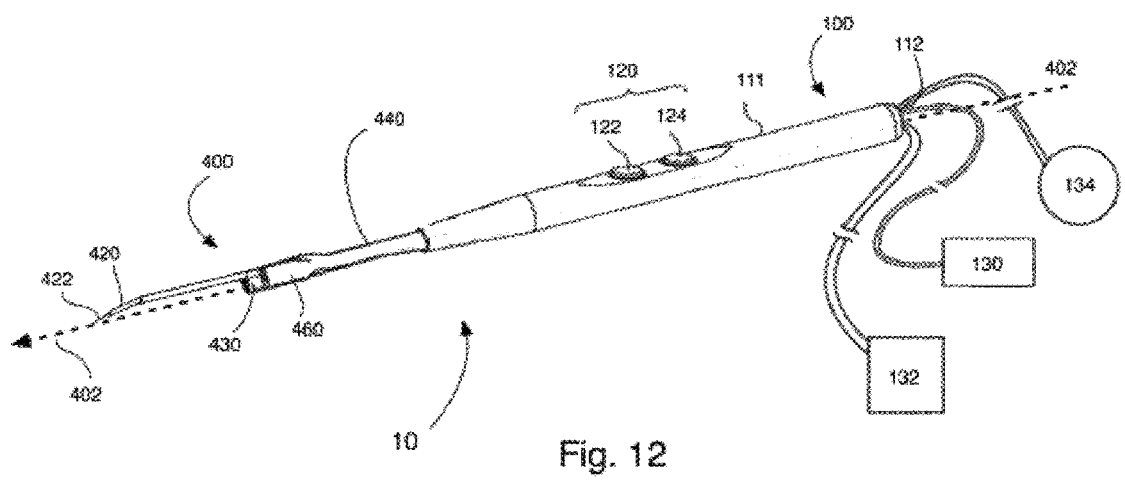
FIG. 12 is a perspective view of an electrocautery device in accordance with an embodiment of the invention having connections to external power sources.
Figure 13:
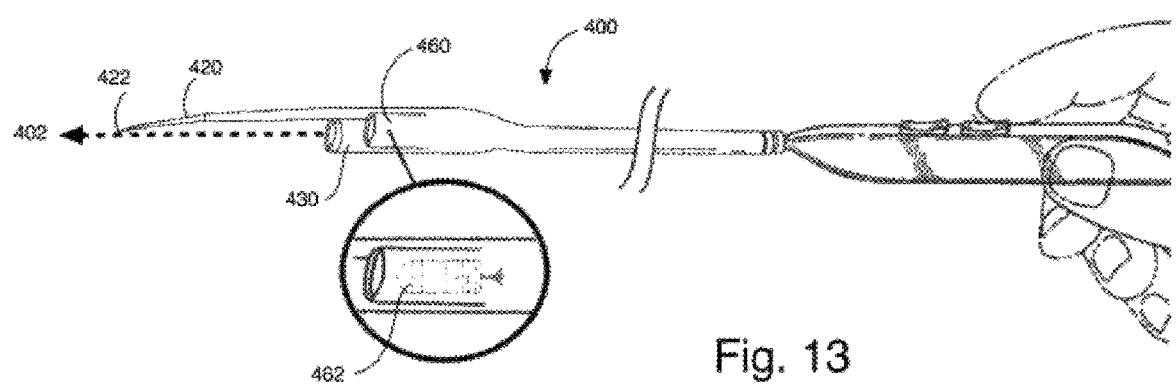
FIG. 13 is a side view of an electrocautery device in accordance with an embodiment of the invention having a camera.
Figure 14:
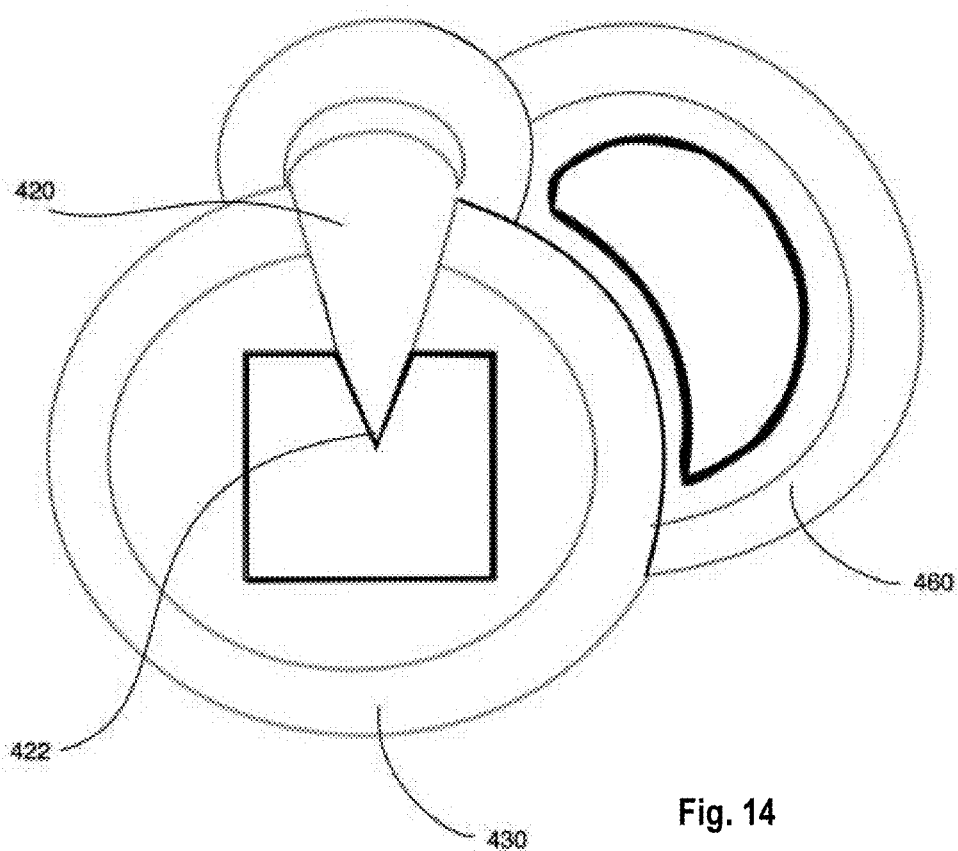
FIG. 14 is front view of the electrocautery device of FIG. 13.
Figure 15:
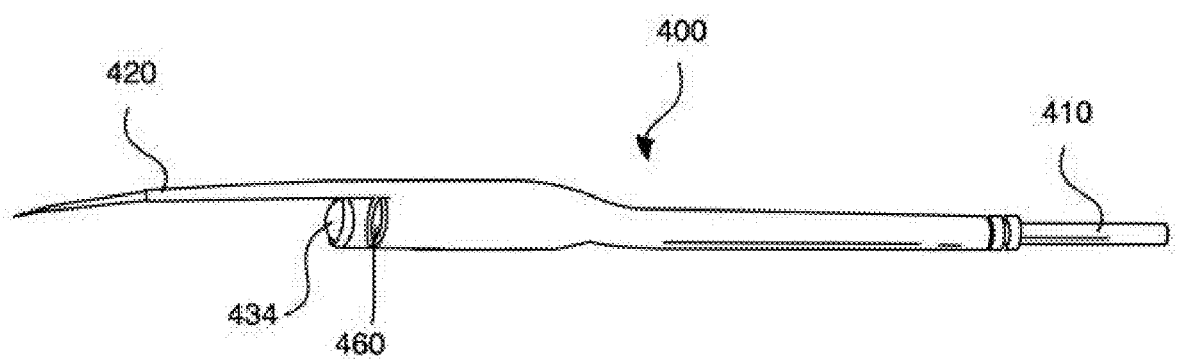
FIG. 15 is a side of an electrode in accordance with an embodiment of the invention having a camera.
Figure 16:
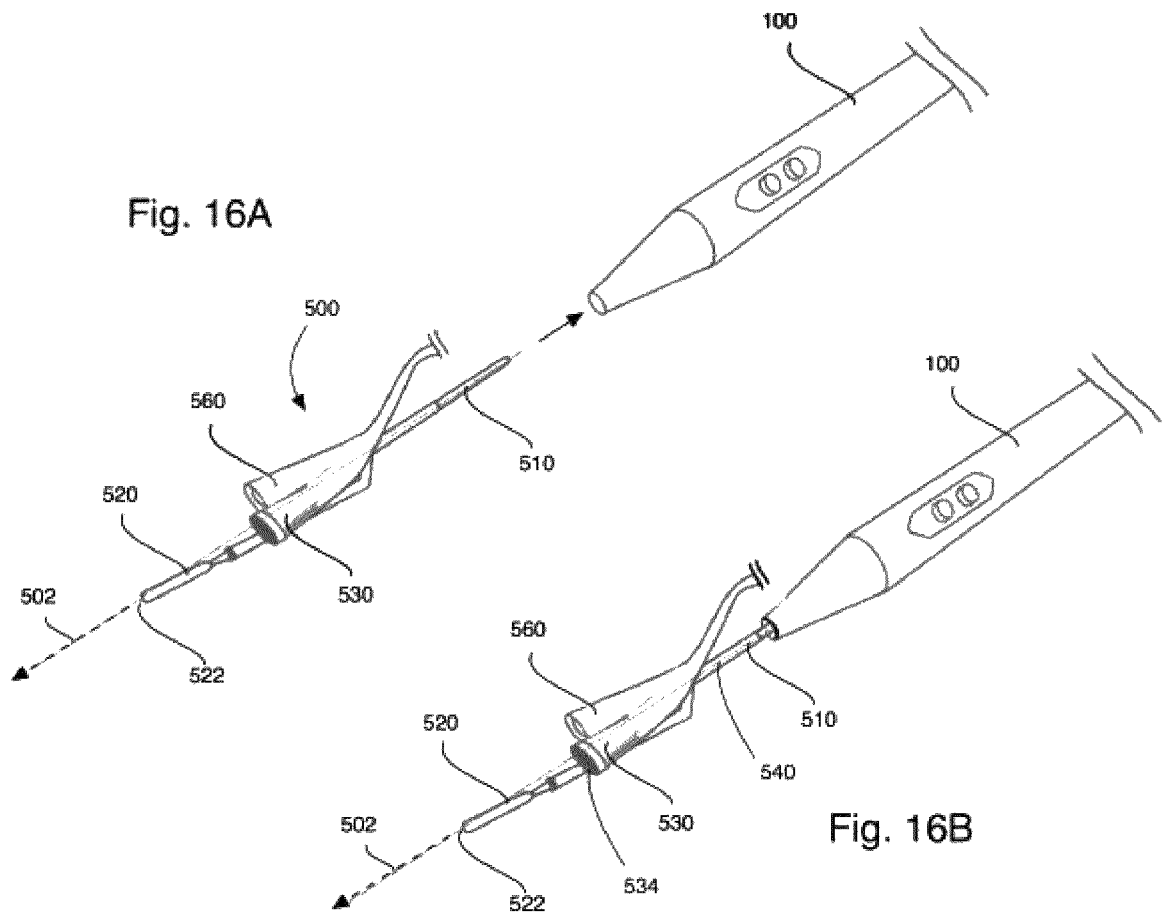

Different electrical currents may be supplied to selectively provide different types of energy for different surgical applications. In the embodiments shown in FIGS. 1-9 and 13-15, once blade unit 200, 400 is connected to handle 100, power may be provided via handle 100 to blade unit 200, 400, for example, via handle coupling element 116. Power may be provided to lighting element 230, 430 from the same power source as electrode 220, 420, namely electrode power source 130. Alternatively, FIGS. 1 and 12 show separate power sources may be provided, electrode power source 130 for electrode 220, 420, and a light power source 132 for lighting element 230, 430.

Alternatively, FIGS. 10-11 and 16A-B show embodiments of blade unit 300, 500 wherein lighting element 230, 430 has an independent light power source 350. The power source 350 may be a building's power source accessible via an outlet, an independent power source, such as a generator, or a smaller, portable power source, such as a battery. Blade unit 300 may include a securing element 352 to secure light power source 350 or a wire or other electrical connection to light power source 350 to handle 100. Alternatively, a portable power source, such as a battery, may be provided within handle 100 to provide power to lighting element without deviating from the scope of the invention.

Certain embodiments of the invention provide one or more relatively small batteries located within blade unit 200, 800, 820, as shown in FIGS. 3 and 21A-22C. FIG. 3 illustrates an embodiment wherein a plurality of batteries 235 is located within or adjacent to light source 230, more specifically, behind light source 232. Therefore, the batteries are located toward the distal end of blade unit 200. FIGS. 21A-22C illustrate embodiments wherein a power source 810, 830 is located toward the proximate end of blade unit 800, 820, more specifically proximate or adjacent to coupling element 802, 822 of blade unit 800, 820. Therefore, when blade unit 800, 820 is coupled to the handle, power source 810, 830 is preferably proximate the middle of the length of the handle-and-unit assembly. More preferably, the weight of the batteries is centered or distributed along the length of the assembly. This may improve balance of the assembly, improve handling of the assembly, and render blade unit 800, 820 less bulky than if a battery were provided toward the distal end of blade unit 800, 820. A blade unit having a portable power source therewithin may improve ease of use, as well as ease of switching blade units in between procedures requiring different surgical electrodes.

Handle 100 may also include a switch element 120 for activating surgical electrode 220, 320, 420, 520. Switch element 120 shown in FIGS. 1 and 12 controls the type of electrical current supplied to electrode tip 222, 322, 422, 522. Switch element 120 preferably comprises buttons 122 and 124, which control the current running through handle 10 and supplied to electrode tip 222, 322, 422, 522, to effect electrocoagulation and/or electrocauterization. One current selection may allow electrode tip 222, 322, 422, 522 to cut; while another current selection may allow electrode tip 222, 322, 422, 522 to perform coagulation. By selecting between buttons 122 and 124, the surgeon may change the tool function from cutting to coagulation easily. A switch for activating lighting element 230, 330, 430, 530 may be provided external to device 10, for example, proximate or on power source 130, 132, 350, along the electrical wire connecting lighting element 230, 330, 430, 530 to power source 130, 132, 350, proximate or on securing element 352 or on lighting element itself.

Camera

Various technologies may also be included in unit 100 not shown in the figures. For example, in certain embodiments of the invention, a camera or other audio-visual technology may be included. The camera may be activated to capture and/or transmit still images or videos to be played on a larger screen live in the operating room or remotely from a different location. This allows not only other doctors to have a better view of what is going on under the skin at the exact surgical site, but may also be used as a training tool for students to follow along and learn by seeing live procedures without crowding the patient or the surgeon. The surgeon need not stop and back away to let others look into the surgical site through the small incision, since they may simply watch the screen, thus also eliminating such delays. Even if the surgeon backs up and lets others look through the incision, it is difficult to do so while the surgeon is performing a procedure, at least partly because of the size and position of the incision, and angle of the surgical site, the surgical instrument inserted therein, etc. Still images or videos may be saved and used post-surgery to document the procedure, use as a teaching aid, performance reviews, for research purposes, etc.

Reference is made to FIGS. 12-16B. Blade unit 100 includes a camera element 460, 560 having a camera positioned proximate lighting element 430, 530, wherein lighting element 230, 330, 430, 530 extends farther toward electrode tip 422, 522. It is preferred for camera element 460, 560 to be proximate electrode tip 422, 522 to minimize obstruction of view caused by blade unit 400, 500, but equidistant or farther from electrode tip 422, 522 than lighting element 430, 500 to eliminate shadowing caused by camera element 460, 560.

Preferably, camera element 460, 560 is substantially small in size as to not obstruct the surgeon's view of the surgical site or hinder the insertion and movement of the blade unit 100 into or within the surgical site. More preferably, camera element 460, 560 has a diameter of less than 1 cm, most preferably less than 0.5 cm. Camera element 460, 560 may include a transmitter 462 to transmit the images or videos being captured by camera element 460, 560 to a remote device, such as a monitor. Transmitter 462 eliminates the need for blade unit 400, 500 and/or device 10 to be wired to the monitor, which may render device 10 easier to control and maneuver. Preferably, transmitter 462 can connect to a WiFi network or other wireless network via which the images or videos may be shared.

Camera element 460, 560 may be powered via handle 100 by an independent camera power source 134, electrode power source 130 or light power source 132. Alternatively, camera element 460, 560 may include a battery therewithin. Other embodiments include, without limitation, camera element 460, 560 powered by light power source 350, or an independent camera power source connected externally to handle 100, proximate a securing element, etc.

Another potential use of an embodiment of blade unit 400, 500 having a camera element is the surgeon being able to conduct the procedure by watching the monitor to see the position of the electrode within the surgical site. Laparoscopic surgery, referred to as minimally invasive surgery, utilizes a laparoscope, a long fiber optic cable system that allows viewing of the affected area by snaking the cable from a more distant, but more easily accessible location. However, laparoscopic surgeries are currently only performed for operations within the abdominal, knee, shoulder, pelvic, thoracic or chest cavity, wherein the cavity is inflated with carbon dioxide to create a working and viewing space. Surgeries like vaginal, plastic surgery, brain, urological and throat procedures are not suitable for laparoscopic surgery. However, by utilizing blade unit 400, 500 having a camera proximate electrode tip 422, 522 and lighting element 430, 530, the surgeon may be able to conduct the procedure while watching the monitor, especially for deeper sites and/or smaller incisions.

Whereas lighting element 230, 330, 430, 530 is illustrated as being built into blade unit 200, 300, 400, 500, it is to be understood that lighting element 230, 330, 430, 530 may be a removable unit that can be attached to an electrode or other part of blade unit 200, 300, 400, 500. For example, lighting element 230, 330, 430, 530 may be attached via, by way of non-limiting example, adhesive, elastic ring, Velcro®, magnetic mechanism or interlocking mechanism. Thus, an existing electrode or other suitable device may be retrofitted in accordance with an embodiment of the invention. Thus, lighting element 230, 330, 430, 530 may be removable or it may become permanently attached to blade unit 200, 300, 400, 500 or other suitable device, as a matter of application-specific design choice. Likewise, camera element 460, 560 may also be a separate component that can be attached, either permanently or removably, to the electrode, blade unit 200, 300, 400, 500 or other suitable device.

Forceps

Figure 19A:
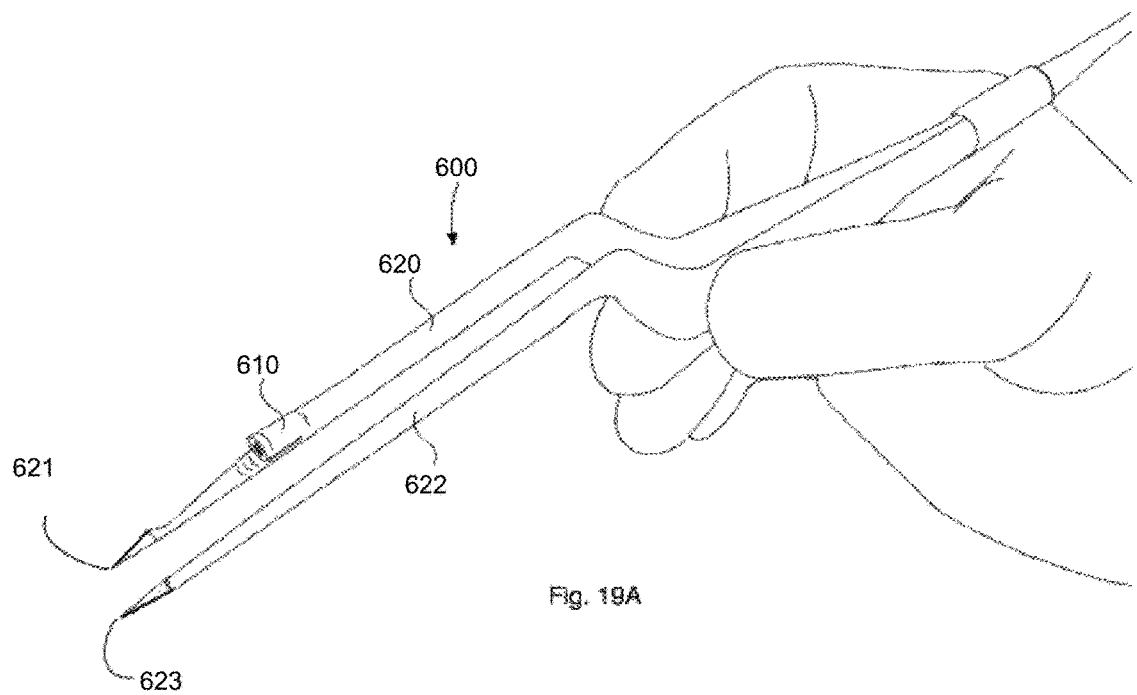
FIG. 19A is a perspective view of a pair of forceps having a light element in accordance with an embodiment of the invention.
Figure 19B:
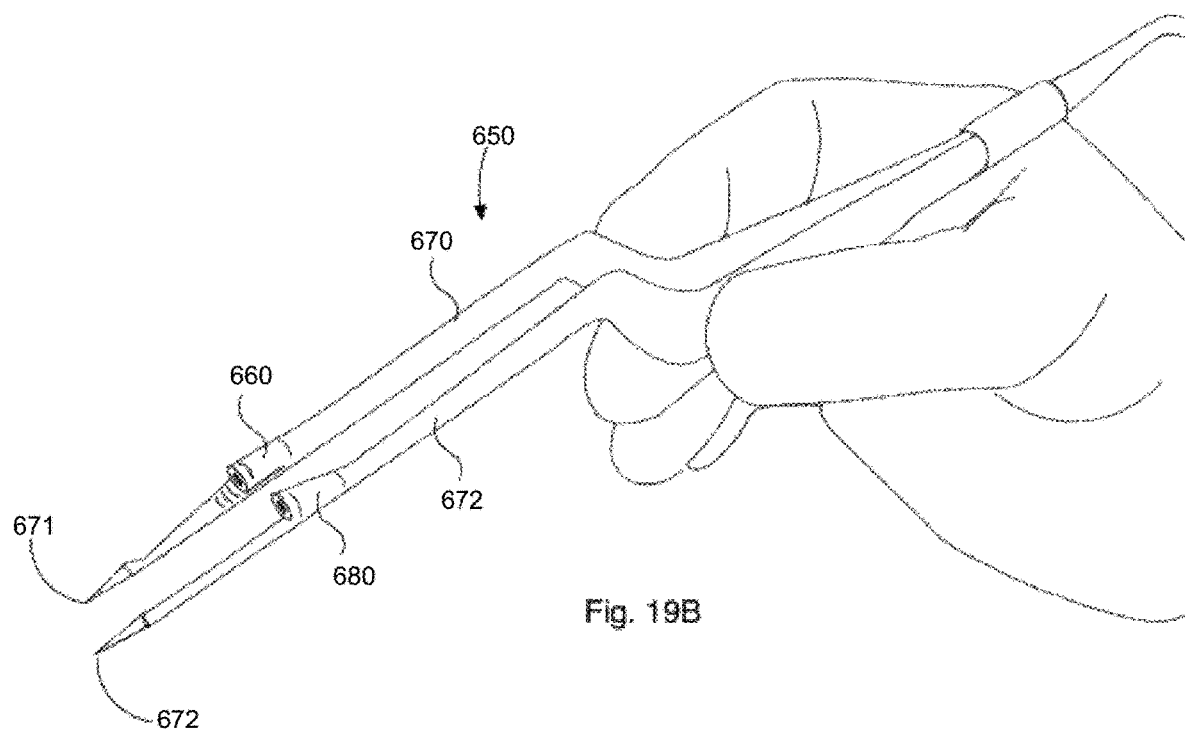
FIG. 19B is showing the forceps of FIG. 19A having a camera.
Figure 20B:
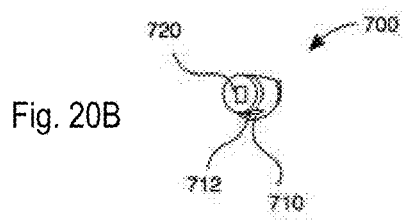
FIG. 20B is a front view of a lighting element for retrofitting in accordance with an embodiment of the invention.
Figure 20C:
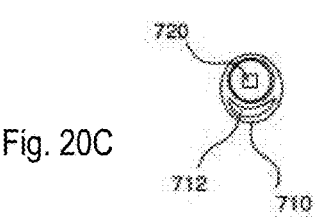
FIG. 20C is a front view of a light element for retrofitting in accordance with an embodiment of the invention.
Figure 20D:
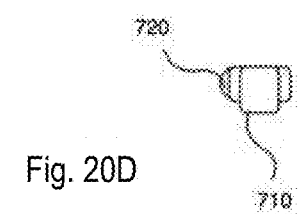
FIG. 20D is a side view of the lighting element of FIG. 20C.
Figure 20A:
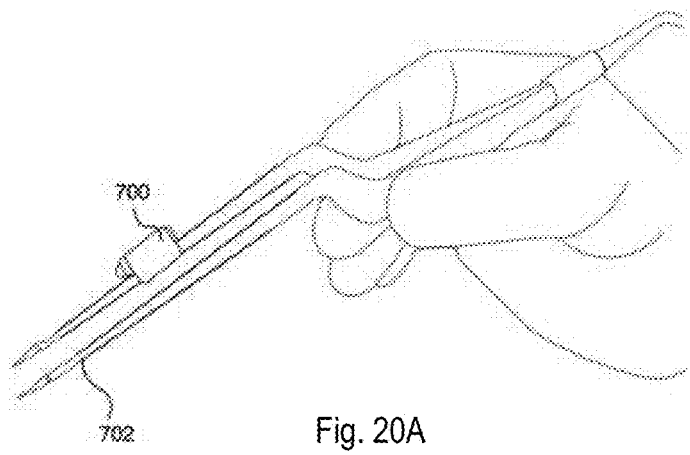
FIG. 20A is a side view of a pair of forceps retrofitted with a lighting element in accordance with an embodiment of the invention.

Reference is made to FIGS. 19A-B in which certain embodiments of forceps 600, 650 include a lighting element 610, 660 positioned proximate tip 621, 671 of first leg 620, 670 preferably less than 5 cm from tip 621, 671. FIG. 19B illustrates an embodiment wherein a camera element 680 is provided on second leg 672, proximate tip 671, preferably less than 5 cm from tip 671. Therefore, light may be provided proximate the site of a procedure wherein an electrocautery device 10 is not being used by utilizing forceps 600, 650. Alternatively, one may provide additional light or camera in addition to that provided by device 200, 300, 400, 500. Preferably, lighting element 610, 660, camera element 680 or both lighting element 610, 660, camera element 680 include a power source, such as one or more batteries, to power the light or camera without the use of wires extending externally. Such an arrangement may make forceps 600, 650 easier to use and less cumbersome. Preferably, the power source is light enough not to significantly weigh down forceps 600, 650. More preferably, lighting element 610, 660 and camera element 680 are similar in weight and are at a similar distance, preferably equidistant, from tip 671, 672.

Illustrated in FIGS. 20A to 20D is an embodiment of a lighting element 700 that may be used to retrofit forceps that do not have a lighting element built in. Lighting element 700 includes a securing element 710 and a light source 720. Securing element 710 secures lighting element 700 to the forceps. In the embodiment shown, securing element 710 comprises an elastic material and may stretch to fit the forceps or any other item to which lighting element 700 is attached. More specifically, one of the legs of the forceps is slid through aperture 712 of securing element 710, until securing element 710 has a stable grip on the leg of the forceps, so that lighting element 700 will not be dislodged unintentionally. Whereas an elastic material is described herein, it is to be understood that any securing element, by way of non-limiting example, adhesive, magnetic or interlocking mechanisms, or Velcro® may be used without deviating from the scope of the invention.

Furthermore, whereas embodiments of lighting element 610, 660, 700 are shown as being positioned on a leg of the forceps, it may be positioned between the forceps legs, for example, along the central axis between the forceps legs, as an alternate embodiment without deviating from the scope of the invention.

Alternate embodiments of the blade unit are shown in FIGS. 21A-22C. As shown, blade unit 800, 820 include a coupling element 802, 822, an electrode 804, 824, and a lighting element 806, 826 surrounding electrode 804, 824. Lighting element may comprise a plurality of LEDs at least partially surrounding electrode 804, 824 such that the collective light emitted therefrom is coaxial with the tip of electrode 804, 824. The embodiment shown in FIG. 21A-21C further includes a suction element 808 for removing smoke or fluids, such as blood, from the surgical site. The device may therefore eliminate the need for a separate suction device during a procedure. A separate suction device may be used for removing smoke formed by tissue being burned at the surgical site, or for removing blood and/or other fluids. Because there is typically only one incision 20, the suction device may crowd the surgical sight as well as the incision 20 through which the surgeon views the surgical site. Therefore, eliminating the need of a separate suction device may facilitate the procedure being performed. Furthermore, because the suction device is integrated with the blade unit, the smoke and/or fluids are removed from proximate the electrode, which is typically the region from which the surgeon wants to remove the smoke and/or fluids, to see the tissue on which he is performing the procedure. If the surgeon holds the suction device, it occupies one of his hands. If another person holds the suction device, the surgeon must tell them when and where to move the suction device, or the person must guess and move the suction device without aim, being careful not to hit the electrode or damaging the tender tissue. Therefore, providing a unitary device that permits the surgeon to illuminate the surgical site, control where the light points, and remove smoke and/or fluids from the surgical site simultaneously while controlling the electrode to perform a procedure may facilitate the procedure and reduce the likelihood of error and surgeon's fatigue.

Lighting element 806, 826 is preferably close to the distal tip of electrode 804, 824, more preferably less than 5 cm therefrom. Additionally, the LEDs surround electrode 804, 824, thus minimizing any shadow cast on the tissue by electrode 804, 824. Whereas three LEDs are illustrated in FIGS. 21A-22C, it is to be understood that the number of LEDs may vary without deviating from the scope of the invention. A camera element may also be included, for example, in place of suction element 808 or next to suction element 808.

The examples provided are merely exemplary, as a matter of application specific to design choice, and should not be construed to limit the scope of the invention in any way. Thus, while there have been shown and described and pointed out novel features of the present invention as applied to preferred embodiments thereof, it will be understood that various omissions and substitutions and changes in the form and details of the disclosed invention may be made by those skilled in the art without departing from the spirit of the invention. For example, camera element 460, 560, 680 may further include an LED or other light source built in without deviating from the scope of the invention as a matter of application specific to design choice.

The apparatus and system may include one or more batteries for powering the entire apparatus or system or separately to each individual component. Additionally, other alterations can be made, as a way of non-limiting example, the shape and size of the surgical electrode, the length of the handle, the length and size of the removable tool, the length and size of the lighting element, can be varied, without deviating from the scope of the invention.

It is the intention, therefore, to be limited only as indicated by the scope of the claims appended hereto.

It is also to be understood that the following claims are intended to cover all of the generic and specific features of the invention herein described and all statements of the scope of the invention, which, as a matter of language, might be said to fall therebetween.

I claim:

1. An electrocautery device comprising:
    a unitary electrocautery unit and a handle;
    wherein said unitary electrocautery unit comprises:
        a body having an elongated shape having a first end and a second end and a unit length therebetween;
        a coupling element disposed at said first end, constructed and arranged to detachably connect to said handle;
        a light element disposed at said second end, constructed and arranged to emit a light having a light central axis;
        a curved side arm jutting radially outward from said body from between said first end and said second end, said side arm having an arm tip extending toward and past said second end and curving toward said light central axis; and
        a surgical electrode extending through and out of said arm tip of said side arm toward said light central axis; and
    wherein said handle comprises a handle body separate and independent from said body of said electrocautery unit, said handle body having a handle length longer than said unit length, said handle body fluffier including a switch for selecting currents provided to said electrode, wherein a first switch selection results in a first current being provided to said electrode, and a second switch selection results in a second current being provided to said electrode.

2. The device of claim 1, wherein said handle is an electrocautery handle.

3. The device of claim 2, wherein said coupling element comprises a protrusion which inserts into an electrode receiving cavity of said electrocautery handle.

4. The electrocautery device of claim 1, wherein said handle is connected to a handle power source providing said first current and said second current to said electrode, and wherein said electrocautery unit includes a light power source separate from and independent of said handle power source, said light power source powering said light element and located externally to said handle.

5. The electrocautery device of claim 1, wherein said handle is connected to a handle power source for providing said first current and said second current to said electrode, and wherein said body of said electrocautery unit houses one or more batteries powering said light element.

6. The electrocautery device of claim 1, wherein said electrocautery unit includes a light switch for activating said light element, said light switch located externally to said handle.

7. The electrocautery unit of claim 1, wherein said electrode is straight.

8. A unitary electrocautery unit for connecting to a handle of an electrocautery device, the electrocautery unit, comprising:
    a body having an elongated shape having a first end and a second end;
    a coupling element disposed at said first end, constructed and arranged to detachably connect to a handle of an electrocautery device;
    a light element disposed at said second end, constructed and arranged to emit a light having a light central axis;
    a curved side arm jutting radially outward from said body from between said first end and said second end, said side arm having an arm tip extending toward and past said second end and curving toward said light central axis; and
    a surgical electrode extending through and out of said arm tip;
    wherein said electrocautery unit does not include a switch for selecting a type of electrical current provided to said surgical electrode;
    wherein said handle of an electrocautery device comprises a handle body having a switch for selecting a type of electrical current provided to said surgical electrode.

9. The electrocautery unit of claim 8, wherein said light element comprises one or more light-emitting diodes.

10. The electrocautery unit of claim 8, wherein said body comprises a body central axis coaxial with said light central axis.

11. The electrocautery unit of claim 8, wherein said electrode comprises a blade for cutting subcutaneous tissue.

12. The electrocautery unit of claim 8, wherein said electrode comprises a probe.

13. The electrocautery unit of claim 8, wherein said electrode is constructed to cauterize subcutaneous tissue.

14. The electrocautery unit of claim 8, wherein said electrocautery unit is permanently fixed to said handle.

15. The electrocautery unit of claim 8, wherein said electrocautery unit further comprises a camera at said second end.

16. The electrocautery unit of claim 15, wherein said electrocautery unit further comprises a transmitter to wirelessly transmit one or more images captured by said camera to a device.

17. The electrocautery unit of claim 16, wherein said transmitter transmits a live feed of one or more images being captured by said camera to a display device.

18. The electrocautery unit of claim 8, wherein said electrocautery unit further comprises a light power source for powering said light element, said light power source being independent of and different from an electrode power source for powering said electrode.

19. The electrocautery unit of claim 8, further comprising a battery;
    wherein the battery is positioned proximate the light unit.

20. The electrocautery unit of claim 8, wherein said surgical electrode comprises an electrode tip extending into and terminating at said light central axis.

21. The electrocautery unit of claim 8, wherein said electrode is straight.

22. The electrocautery unit of claim 8, wherein said body comprises a body central axis coaxial with said light central axis.

23. The electrocautery unit of claim 8, wherein said electrocautery unit further comprises a light switch for activating said light element.

24. A retrofit electrocautery kit compatible with an existing surgical instrument handle, said electrocautery kit comprising:
    an electrocautery unit having an elongated body having
        a first end and a second end, a first connecting element disposed at said first end, constructed and arranged to detachably connect to a distal end of said existing surgical instrument handle, and
        a side arm jutting radially outward from said body, said side arm extending toward said second end and extending radially inward past said second end, said side arm having an arm tip having a second connecting element;
    a light element disposed at said second end, constructed and arranged to emit a light having a light central axis; and
    an electrode having a third connecting element for engaging said second connecting element to connect said electrode to said side arm at said arm tip, wherein said electrode includes an electrode tip extending toward and terminating at said light central axis when said electrode is attached to said side arm, wherein said electrode tip is configured to deliver energy for electrocautery surgery;
    wherein said electrocautery unit does not include a switch for selecting a type of electrical current provided to said electrode.

25. The kit of claim 24, wherein said body further comprises a camera disposed on said second end.

26. The kit of claim 24, further comprising additional electrodes, said additional electrodes including at least one of a blade, a probe, or a cutter.

27. The kit of claim 24, further comprising a surgical instrument handle for connecting to said body, said handle being electrically connected to a power source for powering said electrode.

28. The kit of claim 24, further comprising one or more batteries housed within said body, said one or more batteries being electrically connected to said light element.

29. The kit of claim 24, further comprising a surgical instrument handle for connecting to said body, said handle being longer than said body of said electrocautery unit.

30. An electrocautery device comprising a unitary electrocautery unit and a handle, wherein:
    said unitary electrocautery unit comprises:
        a body having an elongated shape having a first end and a second end and a unit length therebetween;
        a coupling element disposed at said first end, constructed and arranged to detachably connect to said handle;
        a light element disposed at said second end, constructed and arranged to emit a light having a light central axis;
        a side arm jutting radially outward from said body from between said first end and said second end, said side arm having an arm tip extending toward and past said second end toward said light central axis;
        a surgical electrode disposed at said side arm, said surgical electrode extending toward said light central axis; and
        a camera positioned proximate said light element, said camera constructed and arranged to capture images proximate said electrode tip, illuminated by said light element; and
    said, handle comprises a handle body longer than said unit length, said handle body further including a switch for selecting currents provided to said electrode, wherein a first switch selection results in a first current being provided to said electrode, and a second selection switch selection results in a second, current being provided to said electrode.

31. The device of claim 30, wherein said electrode unit is removably attached to said handle.

32. The device of claim 30, wherein said electrode unit includes one or more batteries located within the body of the electrocautery unit to provide electrical power to said light unit and said camera.

* * * * *